(12) United States Patent
Shintani et al.

(10) Patent No.: US 8,336,718 B2
(45) Date of Patent: Dec. 25, 2012

(54) CENTRIFUGAL SEPARATION-USE DEVICE

(75) Inventors: Noriyuki Shintani, Tokyo (JP); Shuji Nosaka, Tokyo (JP); Michihiro Yokokawa, Osaka (JP)

(73) Assignee: Kyocera Medical Corporation, Osaka (JP)

( * ) Notice: Subject to any disclaimer, the term of this patent is extended or adjusted under 35 U.S.C. 154(b) by 1263 days.

(21) Appl. No.: 12/073,878

(22) Filed: Mar. 11, 2008

(65) Prior Publication Data

US 2008/0237115 A1    Oct. 2, 2008

(30) Foreign Application Priority Data

Mar. 26, 2007  (JP) ................. 2007-078891

(51) Int. Cl.
*B01D 21/26*   (2006.01)
(52) U.S. Cl. .......... 210/515; 210/516; 210/518; 494/16; 436/177; 422/548; 422/549; 422/550
(58) Field of Classification Search .......... 210/515, 210/516, 518; 494/16; 436/177; 422/515, 422/516, 518, 548, 549, 550
See application file for complete search history.

(56) References Cited

U.S. PATENT DOCUMENTS 3,687,296 A * 8/1972 Spinosa et al. ............... 210/406

FOREIGN PATENT DOCUMENTS

| JP | 5-501673 A | 4/1993 |
|---|---|---|
| JP | 9-103707 A | 4/1997 |
| JP | 2005-103359 A | 4/2005 |
| JP | 2006-78428 A | 3/2006 |
| JP | 2006-122518 A | 5/2006 |
| WO | WO 91/06373 A1 | 5/1991 |

OTHER PUBLICATIONS

Japanese Office Action issued in corresponding Japanese Patent Application No. 2007-078891, dispatched on Dec. 13, 2011, (with English Translation).

* cited by examiner

*Primary Examiner* — David A Reifsnyder
(74) *Attorney, Agent, or Firm* — Birch, Stewart, Kolasch & Birch, LLP (57) ABSTRACT

The present invention provides a centrifugal separation-use device capable of maintaining a centrifugal separation-use container in a clean state easily at low cost even when centrifugal separation treatment is carried out using a centrifugal separator in an unclean field. A centrifugal separation-use device 1 for collecting a target component by subjecting a solution containing multiple components to centrifugal separation treatment comprises an inner container 10 having a cylindrical section 12 for accommodating the solution and a plug 14 for hermetically sealing the cylindrical section and configured so as to accommodate the solution in a hermetically sealed state, and an outer container 20 having a support section 22 for removably accommodating the cylindrical section and a delivery section 24 for exposing part of the inner container so that the inner container can be removed, and configured so as to accommodate the inner container in a hermetically sealed state.

8 Claims, 7 Drawing Sheets

CENTRIFUGAL SEPARATION-USE DEVICE

BACKGROUND

1. Field of this Invention

The present invention relates to a centrifugal separation-use device for collecting a target component from a liquid, such as blood, containing multiple components by centrifugal separation treatment while its inner container is maintained in a sterilized state.

2. Description of the Prior Art

The blood subjected to centrifugal separation treatment after addition of an anticoagulant is largely separated into three layers, a red blood cell layer, a white blood cell layer and a plasma layer. Since the components contained in the respective separated layers are very useful for living tissue, they are used for various medical treatment methods.

It is known that the platelets contained in the plasma layer release various cytokines including platelet-derived growth factor (PDGF) due to degranulation in the process of a blood coagulation reaction. For this reason, it is attempted to use plasma (platelet-rich plasma: PRP) containing platelets in high concentrations for regenerative medicines (for example, refer to Patent Document 1).

Various methods have been examined as methods for collecting PRP. Specifically speaking, first, primary centrifugal separation treatment with relatively weak centrifugal force is carried out for collected blood. After the centrifugal separation treatment, the red blood cells are localized on the centrifugal side of the rotation and the plasma is present on the center side of the rotation due to the difference in specific gravity of the components. At the boundary between them, plasma containing white blood cells and platelets are present. The plasma corresponding to the supernatant fluid portion, containing the layer of platelets, is transferred to another centrifugal separation-use container. Next, secondary centrifugal separation treatment with relatively strong centrifugal force is carried out to separate the plasma into a PRP layer and a plasma (platelet-poor plasma: PPP) layer containing platelets in low concentrations. Then, the PPP layer corresponding to the supernatant fluid portion is removed to collect the PRP layer. This method in which centrifugal separation treatment is carried out twice is used frequently since the state after the centrifugal separation treatment is satisfactory. Hence, methods for easily collecting PRP using this collection method have been examined variously (for example, refer to Patent Documents 2 and 3).

Furthermore, cells can be fractionated depending on target cell type by subjecting bone marrow fluid and cord blood containing stem cells to centrifugal separation treatment instead of using blood as the liquid to be subjected to centrifugal separation treatment. This method is also used as a regenerative medicine.

[Patent Document 1]
Japanese Patent Application Laid-Open Publication No. 2006-122518
[Patent Document 2]
Japanese Patent Application Laid-Open Publication No. Hei 09-103707
[Patent Document 3]
Japanese Patent Application Laid-Open Publication No. 2006-78428

Various devices have been examined to see if each component is easily subjected to centrifugal separation treatment on the assumption that the devices are sterilized and that the components having been subjected to centrifugal separation treatment are used for medical treatment as a matter of course.

However, when an attempt is made to carry out collection using the above-mentioned method, all the devices are required to be used while being set in a centrifugal separator. Hence, when they are set in the rotor of a centrifugal separator that is not sterilized, their outside-air sides become unclean. Since an operator is required to be kept clean in any operation from the beginning to the end of the operation, an assistant in an unclean field, other than the operator, is required when a collected component is used. Hence, the assistant in the unclean field and the outside-air side of the device in the unclean field become close to the affected area of a patient and may increase the risk of infection in an operation in which a material is embedded. For this reason, there occurs a circumstance in which the use of centrifugal separation treatment is avoided depending on the type of operation.

For the purpose of carrying out centrifugal separation treatment under such a circumstance, the outside-air side of the device is required to be kept clean. As a method for keeping the outside-air side clean, it is conceivable to use a method in which a sterilized bag formed of rolled paper or the like is used. However, since the sterilized bag is insufficient in strength, there is a problem of having a high risk that the sterilized bag is torn when centrifugal separation treatment is carried out. Furthermore, although it is also conceivable to use a method for sterilizing the rotor of a centrifugal separator, there is a problem of imposing quite a burden when the rotor of a large-size centrifugal separator is sterilized for each operation. Moreover, although it is further conceivable to use a method for automatically carrying out centrifugal separation treatment under a sterile environment using an automated centrifugal separator or the like, there is a problem of the very high cost of the centrifugal separator.

SUMMARY OF THIS INVENTION

Accordingly; in order to solve the technical problems described above, the present invention is intended to provide a centrifugal separation-use device capable of maintaining a centrifugal separation-use container in a clean state easily at low cost even when centrifugal separation treatment is carried out using a centrifugal separator in an unclean field.

To solve the technical problems described above, the present invention provides a centrifugal separation-use device described below.

More specifically, the centrifugal separation-use device according to the present invention for collecting a target component by subjecting a solution containing multiple components to centrifugal separation treatment comprises:

an inner container having a cylindrical section for accommodating the solution and a plug for hermetically sealing the cylindrical section and configured so as to accommodate the solution in a hermetically sealed state, and an outer container having a support section for removably accommodating the cylindrical section and a delivery section for exposing part of the inner container so that the inner container can be removed, and configured so as to accommodate the inner container in a hermetically sealed state.

With the above-mentioned configuration, the inner container in a clean state is accommodated in the outer container in a hermetically sealed state. Hence, even if the outer container accommodating the inner container is subjected to centrifugal separation treatment in an unclean field, the inner container is not affected by the unclean state, and the inner container is maintained in the clean state. After the centrifugal separation treatment, an assistant or the like in the unclean field opens the outer container, and an operator in a clean field handles the inner container that is maintained in the clean state. Hence, the inner container is maintained in the clean state.

The operator and the assistant are accustomed to the work for removing contents by separating the cover sections of packaging containers in the right and left directions. Hence, it is preferable that the lower end of the delivery section is secured to the support section and that the delivery section extending from its lower end to its upper end is divided into two parts in the longitudinal direction of the support section so as to have a hinge structure that can be opened in the right and left directions.

It is also possible to have a configuration in which the delivery section of the outer container is separated in the up and down directions, instead of separating the delivery section of the outer container in the right and left directions. In other words, the delivery section is configured so as to be separate from the support section and capable of being engaged with the support section.

It is further possible that the support section is configured so as not only to accommodate one inner container but also to accommodate multiple inner containers disposed in parallel.

Since the outer container is subjected to large centrifugal force during centrifugal separation treatment, the outer container is required to be configured so as not to be deformed or broken by the centrifugal force. Although it is effective to increase the thickness of the side wall of the outer container in order to prevent deformation and breakage, this results in increasing the size of the outer container. It is thus preferable that the outer container is made of a self-shape retaining material so as not to be deformed by centrifugal force.

The present invention is applicable to the case that the solution is blood, although the present invention is also applicable to bone marrow fluid and cord blood containing stem cells. Furthermore, the present invention is further applicable to the case that stem cells contained in fat, skin and various organs are separated from the other cells.

In the case that the solution to be treated is blood, the target component is platelet-rich plasma. Furthermore, in the case that the solution to be treated is bone marrow fluid, the target component is stem cells.

DESCRIPTION OF THE PREFERRED EMBODIMENTS

A first embodiment of a centrifugal separation-use device 1 according to the present invention will be described below in detail referring to FIGS. 1A and 1B to 5.

Figure 1A:
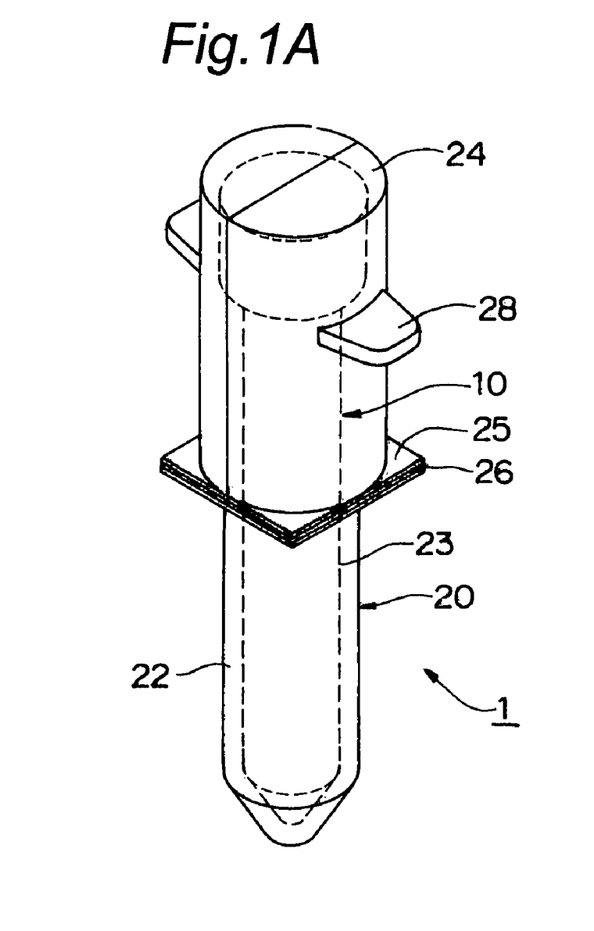
FIGS. 1A and 1B are perspective views schematically showing a centrifugal separation-use device according to a first embodiment of the present invention, FIG. 1A showing a state where a door section is closed, and FIG. 1B showing a state where the door section is open.
Figure 1B:
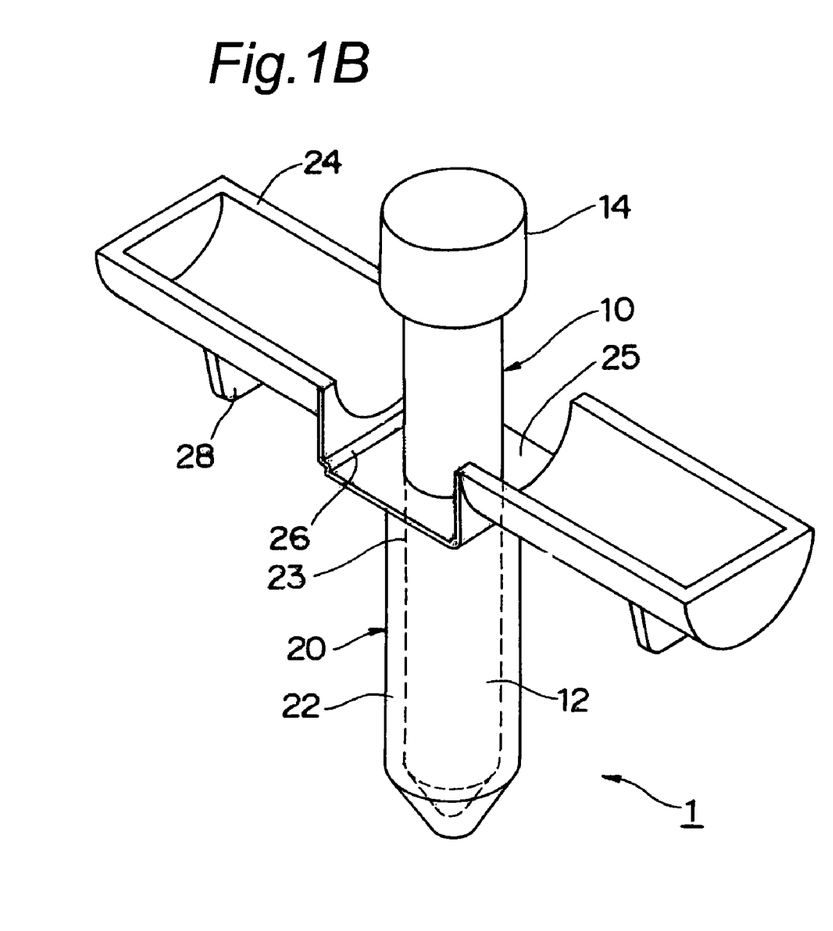
Figure 2:
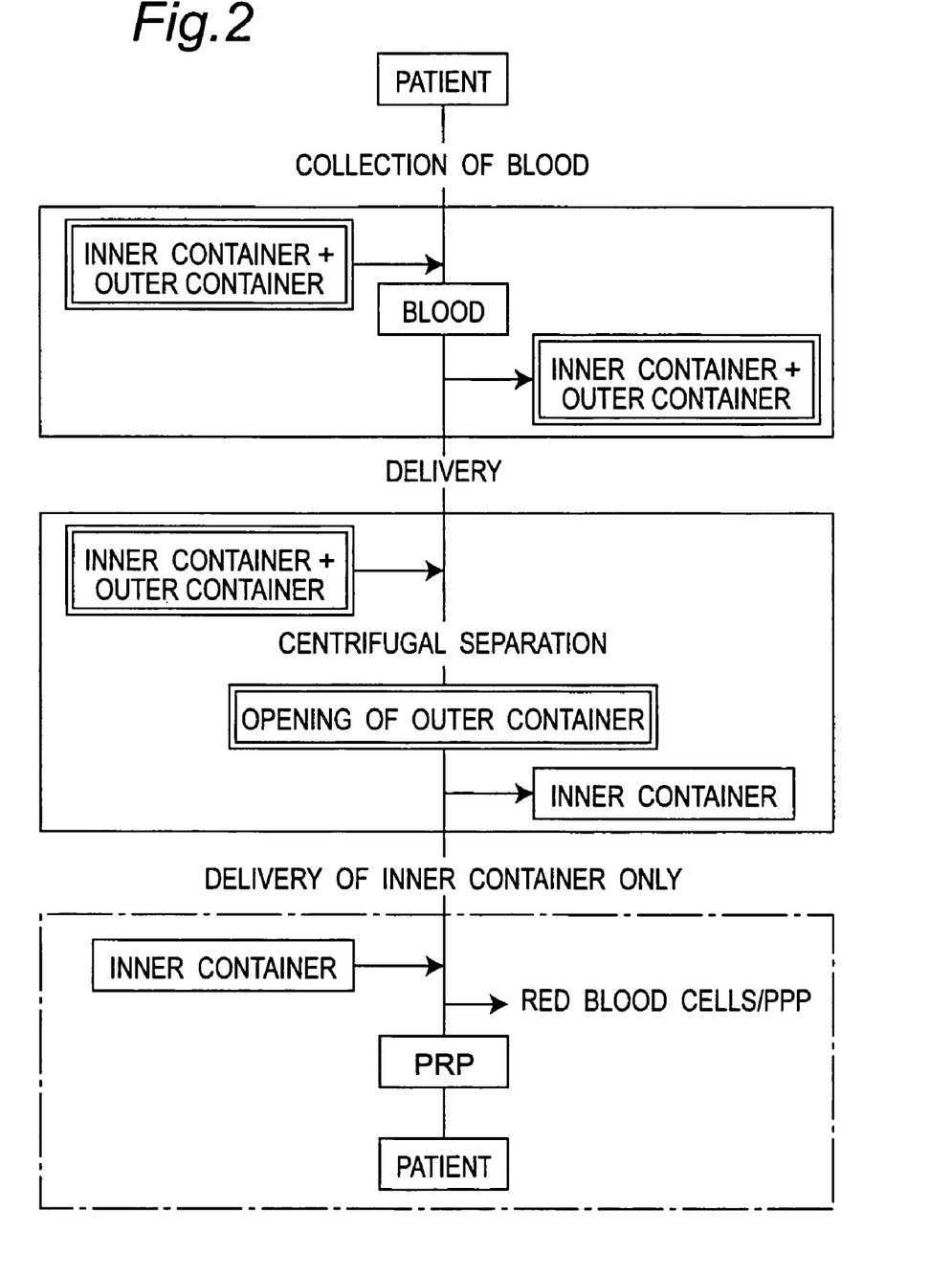
FIG. 2 is a flowchart showing a centrifugal separation process performed when the centrifugal separation-use device according to the present invention is used to collect platelet-rich plasma from blood.
Figure 3:
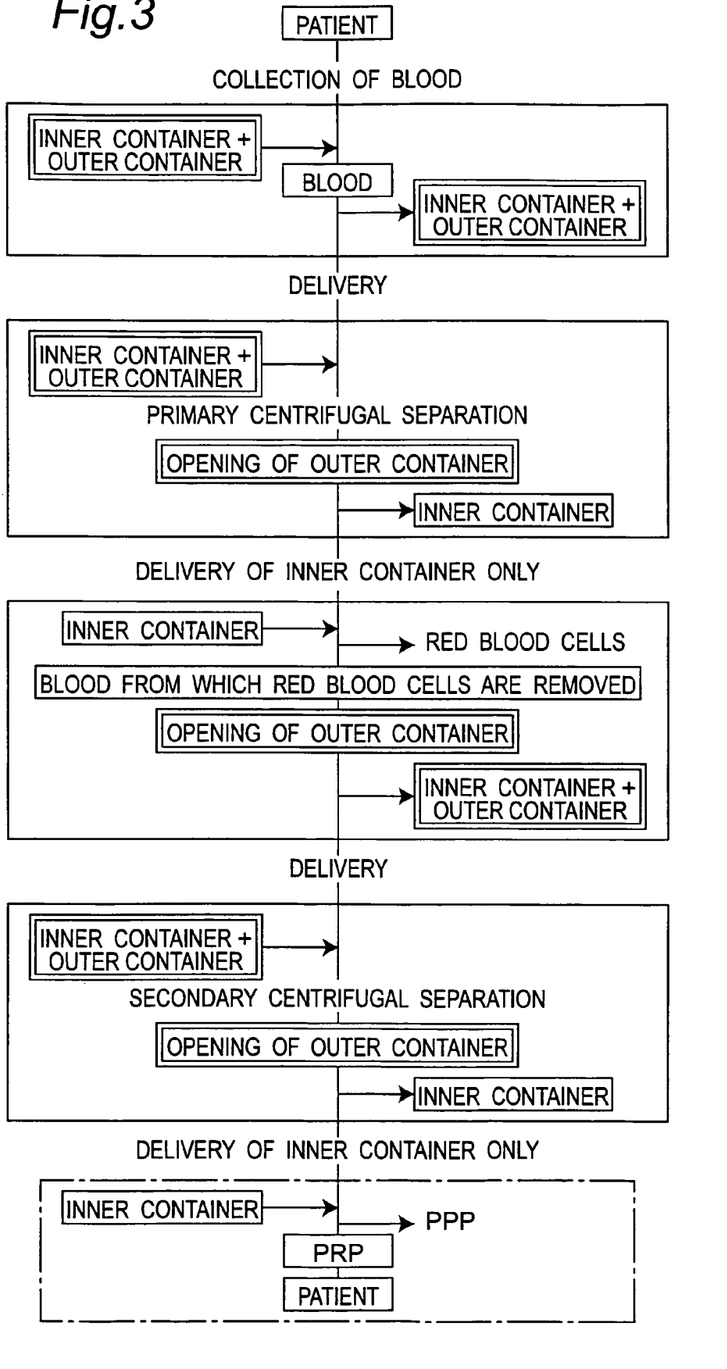
FIG. 3 is a flowchart showing another centrifugal separation process performed when the centrifugal separation-use device according to the present invention is used to collect platelet-rich plasma from blood.
Figure 4:
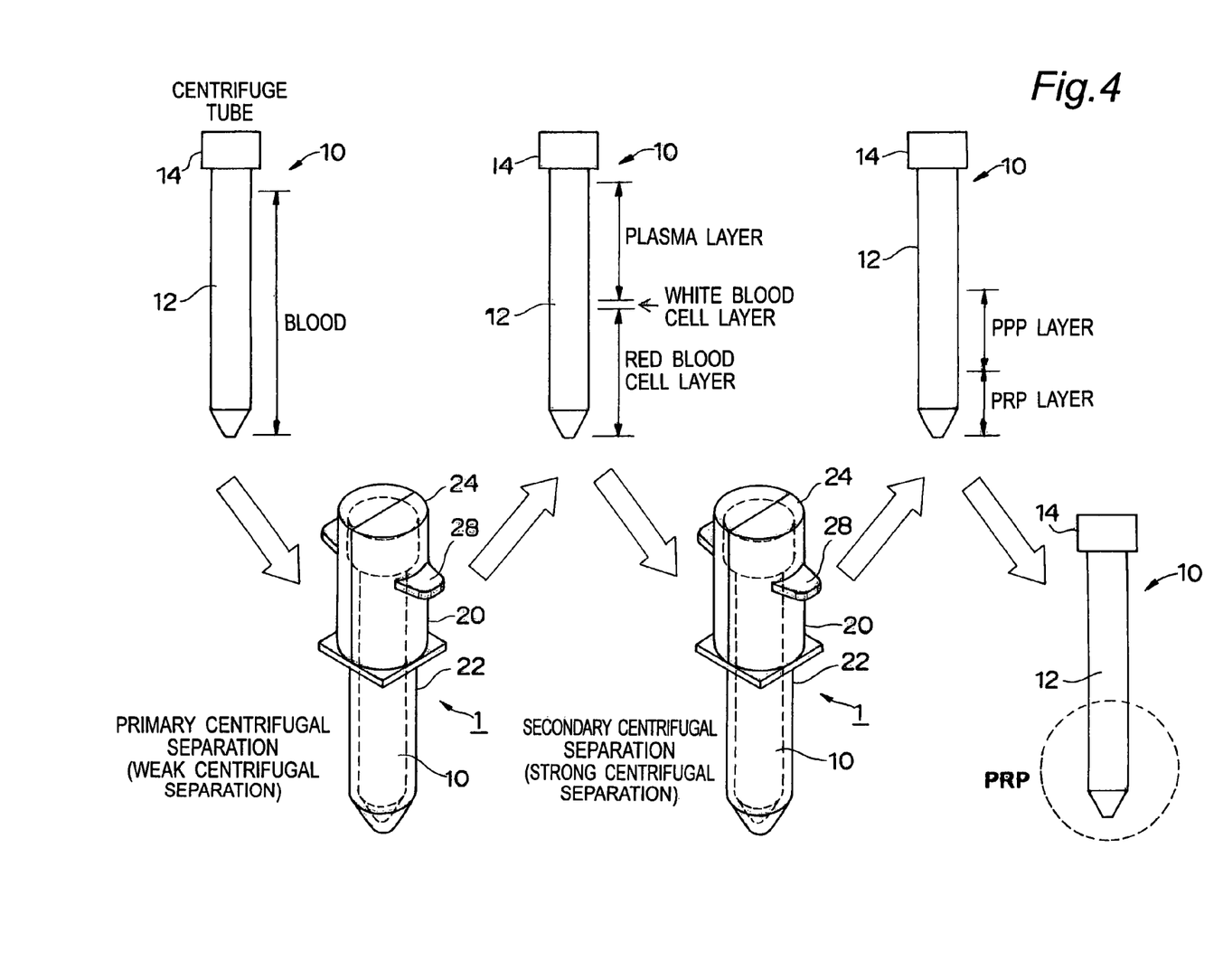
FIG. 4 is a view schematically illustrating the centrifugal separation process shown in FIG. 3.
Figure 5:
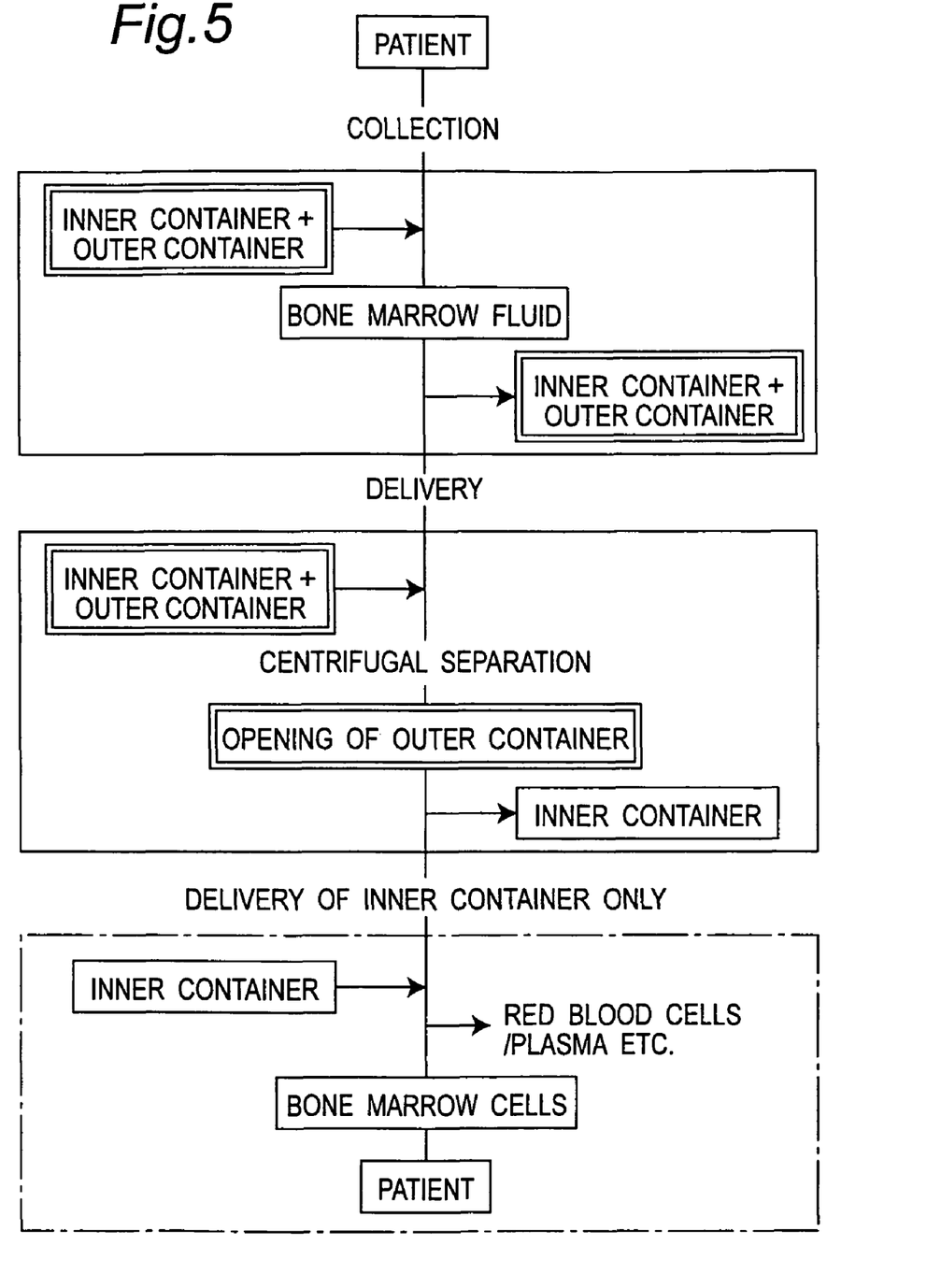
FIG. 5 is a flowchart showing still another centrifugal separation process performed when the centrifugal separation-use device according to the present invention is used to collect bone marrow cells from bone marrow fluid.

FIGS. 1A and 1B are perspective views schematically showing the centrifugal separation-use device 1 according to the first embodiment of the present invention. FIG. 1A shows a state where a door section 24 is closed, and FIG. 1B shows a state where the door section 24 is open. FIG. 2 is a flowchart showing a centrifugal separation process performed when the centrifugal separation-use device 1 according to the present invention is used to collect platelet-rich plasma from blood. FIG. 3 is a flowchart showing another centrifugal separation process performed when the centrifugal separation-use device 1 according to the present invention is used to collect platelet-rich plasma from blood. FIG. 4 is a view schematically illustrating the centrifugal separation process shown in FIG. 3. FIG. 5 is a flowchart showing still another centrifugal separation process performed when the centrifugal separation-use device 1 according to the present invention is used to collect bone marrow cells from bone marrow fluid.

First, the configuration of the centrifugal separation-use device 1 will be described referring to FIGS. 1A and 1B.

The centrifugal separation-use device 1 comprises a sample tube (inner container) 10 for accommodating a sample solution containing a target component in a hermetically sealed state and an adaptor container (outer container) 20 for accommodating the sample tube 10 in a hermetically sealed state.

The sample tube 10 serving as an inner container has an opening at its top and a tapered closed bottom section at its bottom, and is equipped with a cylindrical section 12 for accommodating a sample solution, such as blood, bone marrow fluid or cord blood, and a plug 14 fitted in the opening at the top to hermetically seal the cylindrical section 12. The sample tube 10 is sterilized.

The adaptor container 20 serving as an outer container is configured so as to be installable in a centrifugal separator and is equipped with a support section 22 and the door section (delivery section) 24. The support section 22 of the adaptor container 20 has an opening at its top and a tapered closed bottom section at its bottom and removably accommodates the cylindrical section 12 via an insertion hole 23. The door section (delivery section) 24 of the adaptor container 20 allows part of the sample tube 10 to be exposed so that the sample tube 10 can be inserted and removed. In the state that the sample tube 10 is accommodated in the adaptor container 20, the whole of the plug 14 of the sample tube 10 is exposed, and the upper part of the cylindrical section 12, that is, 30 to 70% of the whole length thereof, is exposed.

The door section 24 serving as a delivery section is secured to the flange section 25 of the support section 22 via hinge sections 26 formed into a thin-walled configuration at the lower end section of the door section 24. In addition, the door section 24 is divided into two pieces in the longitudinal direction of the support section 22 from the lower end section to the upper end section, that is, in the axial direction, and a hinge structure that can be opened/closed in the right and left directions is formed. A knob section 28 is formed on each of the right and left side faces of the door section 24. The knob sections 28 may be equipped with slip-proof means, such as projections and depressions or grooves, so that an assistant or the like can easily hold the knob sections 28. Furthermore, the knob sections 28 may be colored to a color different from those of the other sections so that the assistant or the like can easily recognize the existence of the knob sections 28. Moreover, the door section 24 can be divided into right and left pieces evenly or unevenly.

The right and left pieces of the door section 24 are configured so as to form an engagement structure so that the right and left pieces can be engaged with each other and so that the door section 24 does not open unintentionally when the adaptor container 20 is handled or subjected to centrifugal separation treatment. Various known structures can be used for this kind of engagement structure. Examples of such a structure include a structure having convex and concave sections fitted to each other, a thread engagement structure, a structure having an elastically deformable pawl and a concave section or a groove fitted to each other, and a structure having a pair of embedded magnets attracting each other. Hence, when centrifugal separation treatment is carried out, the door section 24 is closed by the function of the engagement structure as shown in FIG. 1A. When the sample tube 10 is removed, the engagement of the engagement structure is released, and the door section 24 is open as shown in FIG. 1B.

The adaptor container 20 is configured so as to be able to withstand centrifugal force during centrifugal separation treatment. Since the space inside the centrifugal separator is limited, it is not preferable to use the adaptor container 20 that is formed of rolled paper or the like having a thick wall. Resin or metal materials are preferable as self-shape retaining materials that can withstand centrifugal force during centrifugal separation treatment even if the wall thereof is not made very thick. More specifically, it is possible to use thermoplastic resins, such as ABS resins, acrylic resins, polypropylene resins, polystyrene resins, polyacetal resins, polyamide resins, polycarbonate resins and polyethylene terephthalate resins. Furthermore, it is possible to use metal materials, such as stainless steel, copper and aluminum.

It is possible to use foamed resins, such as polyurethane resins and polyethylene resins, and elastic materials, such as silicone rubber, nitrile rubber and fluororubber, to enhance the hermetic sealing effect of the door section 24.

Next, the procedure of how to use the above-mentioned centrifugal separation-use device 1 will be described referring to FIGS. 2 to 5.

FIG. 2 shows a centrifugal separation process that is carried out when platelet-rich plasma (PRP) is collected from blood. The areas enclosed with a solid line indicate that work is carried out in a general environment with gloves on (in an unclean field). The area enclosed with an alternate long and short dashed line indicates that work is carried out in a sterilized environment with gloves on (in a clean field). The area "inner container+outer container" enclosed with double lines indicates that the sample tube 10 is inserted in the adaptor container 20. The area "inner container" enclosed with a single line indicates that the sample tube 10 is used independently.

After blood is collected from a patient, the plug 14 of the sterilized sample tube 10 is opened, and the collected blood is poured into the sample tube 10 inside the adaptor container 20 in the unclean field. Then, the plug 14 of the sample tube 10 is closed, and the door section 24 of the adaptor container 20 is closed to hermetically seal the sample tube 10 inside the adaptor container 20. The sample tube 10 being hermetically sealed inside the adaptor container 20 is delivered to the centrifugal separation process.

Although the centrifugal separation process is carried out in the unclean field, since centrifugal separation treatment is carried out in a state that the sample tube 10 is hermetically sealed inside the adaptor container 20, the sample tube 10 is prevented from being contaminated. After the centrifugal separation treatment, the assistant or the like in the unclean field holds the knob sections 28 of the adaptor container 20 being exposed to the unclean field and opens the door section 24 of the adaptor container 20. Only the sample tube 10 exposed from the adaptor container 20 is delivered to an operator.

The operator in the clean field holds the exposed sample tube 10, opens the plug 14 of the sample tube 10, removes red blood cells and platelet-poor plasma (PPP) from the centrifuged blood to collect the target platelet-rich plasma (PRP) and applies the platelet-rich plasma to the patient. The collected platelet-rich plasma (PRP) is used, for example, to repair the tendons and ligaments in various parts of the body, to heal wounds and to regenerate bones by virtue of the natural healing power of the platelets.

Next, another centrifugal separation process will be described referring to FIGS. 3 and 4. FIG. 3 shows another centrifugal separation process that is carried out when platelet-rich plasma (PRP) is collected from blood by two-step centrifugal separation treatment. FIG. 4 schematically shows the centrifugal separation process shown in FIG. 3.

After blood is collected from a patient, the plug 14 of the sterilized sample tube 10 is opened, and the collected blood is poured into the sample tube 10 inside the adaptor container 20 in the unclean field. Then, the plug 14 of the sample tube 10 is closed, and the door section 24 of the adaptor container 20 is closed to hermetically seal the sample tube 10 inside the adaptor container 20. The sample tube 10 being hermetically sealed inside the adaptor container 20 is delivered to a primary centrifugal separation process.

Although the primary centrifugal separation process is carried out in the unclean field, since primary centrifugal separation treatment is carried out in a state that the sample tube 10 is hermetically sealed inside the adaptor container 20, the sample tube 10 is prevented from being contaminated. After the primary centrifugal separation treatment, the assistant or the like in the unclean field holds the knob sections 28 of the adaptor container 20 being exposed to the unclean field and opens the door section 24 of the adaptor container 20. Only the sample tube 10 exposed from the adaptor container 20 is delivered to the operator.

The operator in the clean field holds the exposed sample tube 10, opens the plug 14 of the sample tube 10, removes red blood cells from the centrifuged blood. The blood from which red blood cells were removed is transferred to another sterilized sample tube 10. Then, the plug 14 of the sample tube 10 is closed, and the door section 24 of the adaptor container 20 is closed to hermetically seal the sample tube 10 inside the adaptor container 20. The sample tube 10 being hermetically sealed inside the adaptor container 20 is delivered to a secondary centrifugal separation process.

Although the secondary centrifugal separation process is carried out in the unclean field, since secondary centrifugal separation treatment is carried out in a state that the sample tube 10 is hermetically sealed inside the adaptor container 20, the sample tube 10 is prevented from being contaminated. After the secondary centrifugal separation treatment, the assistant or the like in the unclean field holds the knob sections 28 of the adaptor container 20 being exposed to the unclean field and opens the door section 24 of the adaptor container 20. Only the sample tube 10 exposed from the adaptor container 20 is delivered to the operator.

The operator in the clean field holds the exposed sample tube 10, opens the plug 14 of the sample tube 10, removes platelet-poor plasma (PPP) from the centrifuged blood to collect the target platelet-rich plasma (PRP) and applies the platelet-rich plasma to the patient.

Next, still another centrifugal separation process will be described referring to FIG. 5. FIG. 5 shows a centrifugal separation process that is carried out when bone marrow cells are collected from bone marrow fluid by centrifugal separation treatment.

After bone marrow fluid is collected from a patient, the plug 14 of the sterilized sample tube 10 is opened, and the collected bone marrow fluid is poured into the sample tube 10 inside the adaptor container 20 in the unclean field. Then, the plug 14 of the sample tube 10 is closed, and the door section 24 of the adaptor container 20 is closed to hermetically seal the sample tube 10 inside the adaptor container 20. The sample tube 10 being hermetically sealed inside the adaptor container 20 is delivered to the centrifugal separation process.

Although the centrifugal separation process is carried out in the unclean field, since centrifugal separation treatment is carried out in a state that the sample tube 10 is hermetically sealed inside the adaptor container 20, the sample tube 10 is prevented from being contaminated. After the centrifugal separation treatment, the assistant or the like in the unclean field holds the knob sections 28 of the adaptor container 20 being exposed to the unclean field and opens the door section 24 of the adaptor container 20. Only the sample tube 10 exposed from the adaptor container 20 is delivered to the operator.

The operator in the clean field holds the exposed sample tube 10, opens the plug 14 of the sample tube 10, removes red blood cells, plasma, etc. from the centrifuged bone marrow fluid to collect the target bone marrow cells and applies the bone marrow cells to the patient.

Figure 6A:
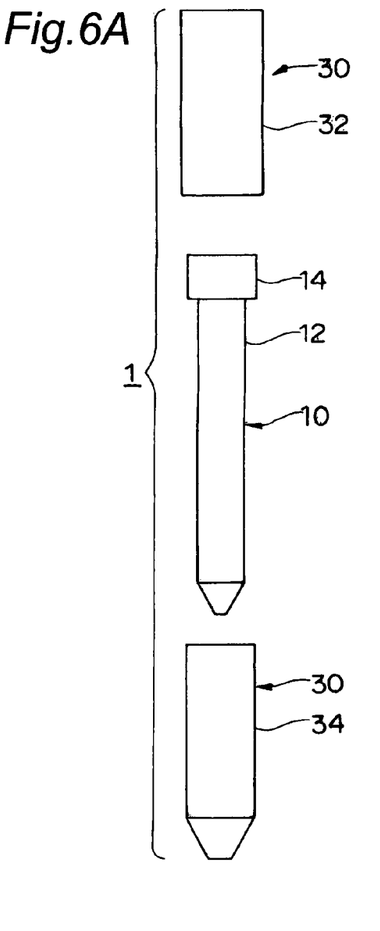
FIGS. 6A to 6D schematically show a centrifugal separation-use device according to a second embodiment of the present invention, FIG. 6A showing a state where an inner container is completely removed from an outer container, FIG. 6B showing a state where the inner container is accommodated in the support section of the outer container, FIG. 6C showing a state where the inner container is completely accommodated in the outer container, and FIG. 6D being a perspective view of FIG. 6B.
Figure 6B:
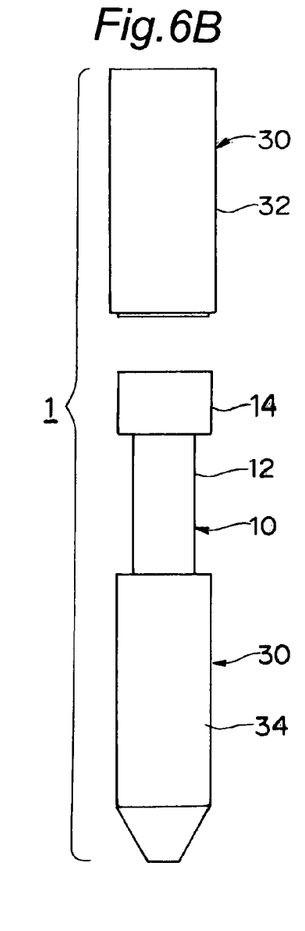
Figure 6C:
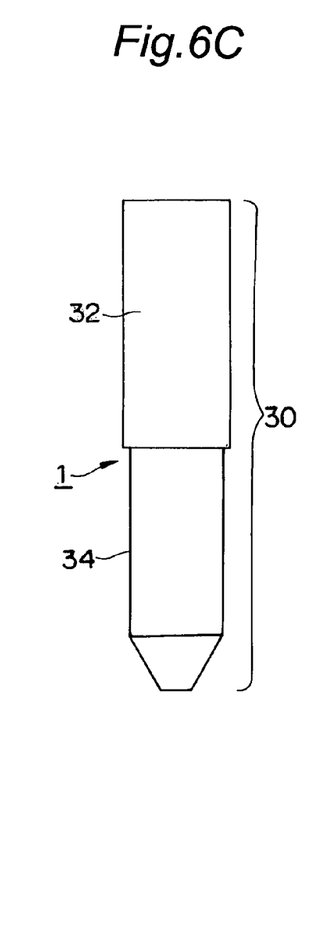
Figure 6D:
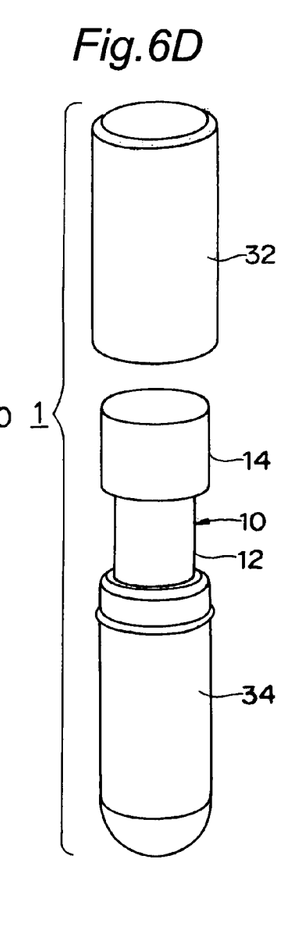
Figure 7:
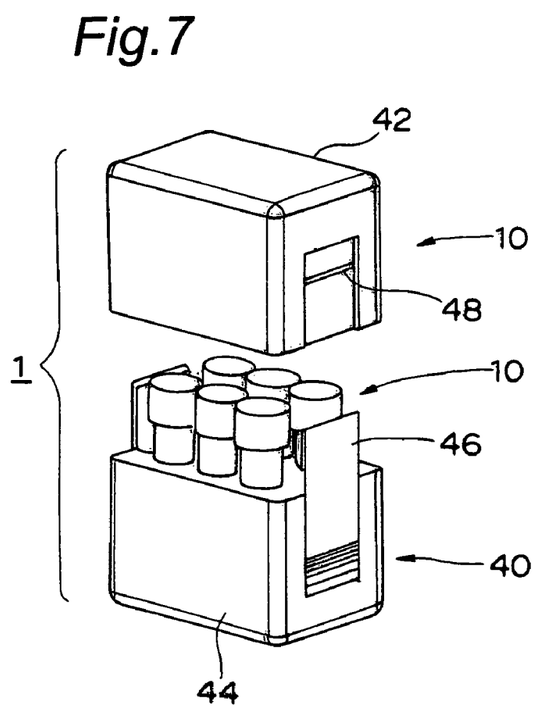
FIG. 7 is a view schematically showing a centrifugal separation-use device according to a third embodiment of the present invention.

Next, other embodiments of the centrifugal separation-use device 1 will be described below. FIGS. 6A to 6D schematically show a centrifugal separation-use device 1 according to a second embodiment of the present invention. FIG. 7 schematically shows a centrifugal separation-use device 1 according to a third embodiment of the present invention. The differences between the centrifugal separation-use devices 1 according to the second and third embodiments and the centrifugal separation-use device 1 according to the first embodiment described above will be mainly described below.

The centrifugal separation-use device 1 shown in FIGS. 6A to 6D has a configuration in which the upper cap (delivery section) 32 of an adaptor container (outer container) 30 is separated upward from a support section 34. In other words, the upper cap 32 serving as a delivery section is configured so as to be separate from the support section 34 and engaged with the support section 34.

The adaptor container 30 serving as an outer container is configured so as to be installable in a centrifugal separator and is equipped with the support section 34 and the upper cap 32. The support section 34 of the adaptor container 30 has an opening at its top and a tapered closed bottom section at its bottom and removably accommodates a cylindrical section 12 via an insertion hole. The upper cap 32 of the adaptor container 30 allows part of a sample tube 10 to be exposed so that the sample tube 10 can be inserted and removed. In the state that the sample tube 10 is accommodated in the adaptor container 30, the whole of the plug 14 of the sample tube 10 is exposed, and the upper part of the cylindrical section 12, that is, 30 to 70% of the whole length thereof, is exposed.

The support section 34 and the upper cap 32 are configured so as to form an engagement structure so that the upper cap 32 is not separated unintentionally when the adaptor container 30 is handled or subjected to centrifugal separation treatment. Various known structures can be used for this kind of engagement structure. Examples of such a structure include a structure having convex and concave sections fitted to each other, a thread engagement structure, a structure having an elastically deformable pawl and a concave section or a groove fitted to each other, and a structure having a pair of embedded magnets attracting each other. Hence, when the sample tube 10 is removed, the engagement of the engagement structure is released, and the upper cap 32 is separated as shown in FIG. 6B. When centrifugal separation treatment is carried out, the upper cap 32 is closed by the function of the engagement structure as shown in FIG. 6C.

The adaptor container 30 is also formed of a self-shape retaining resin or metal material that can withstand centrifugal force during centrifugal separation treatment. More specifically, it is possible to use thermoplastic resins, such as ABS resins, acrylic resins, polypropylene resins, polystyrene resins, polyacetal resins, polyamide resins, polycarbonate resins and polyethylene terephthalate resins. Furthermore, it is possible to use metal materials, such as stainless steel, copper and aluminum.

It is also possible to use foamed resins, such as polyurethane resins and polyethylene resins, and elastic materials, such as silicone rubber, nitrile rubber and fluororubber, to enhance the hermetic sealing effect of the upper cap 32.

The centrifugal separation-use device 1 shown in FIG. 7 has a configuration in which the upper cover (delivery section) 42 of an adaptor container (outer container) 40 is separated upward from a support section 44 and multiple sample tubes 10 can be accommodated. In other words, a tray having multiple insertion holes disposed so as to be aligned in the lateral and longitudinal directions is attached to the support section 44. The adaptor container 40 serving as an outer container is configured so as to be installable in a centrifugal separator and equipped with the support section 44 and the upper cover 42. The upper cover 42 serving as a delivery section is configured so as to be separate from the support section 44. The engagement hook 46 of the support section 44 is engaged with the engagement groove 48 of the upper cover 42, whereby the upper cover 42 is engaged with the support section 44. As the engagement structure, those similar to the engagement structures described above can be used.

The invention claimed is:

1. A centrifugal separation-use device for collecting a target component by subjecting a solution containing multiple components to centrifugal separation treatment comprising:
    an inner container having a cylindrical section for accommodating said solution and a plug for hermetically sealing said cylindrical section and configured so as to accommodate said solution in a hermetically sealed state, and
    an outer container having a support section for removably accommodating said cylindrical section and a delivery section for exposing part of said inner container so that said inner container can be removed, and configured so as to accommodate said inner container in a hermetically sealed state;
    wherein said delivery section is configured so as to be separate from said support section and capable of being engaged with said support section; and wherein 30 to 70% of the length of the cylindrical section is exposed when the delivery section is opened.

2. The centrifugal separation-use device according to claim 1, wherein the lower end of said delivery section is secured to said support section, and said delivery section extending from the lower end to the upper end thereof is divided into two parts in the longitudinal direction of said support section so as to have a hinge structure that can be opened in the right and left directions.

3. The centrifugal separation-use device according to claim 1, wherein said support section is configured so as to accommodate multiple inner containers disposed in parallel.

4. The centrifugal separation-use device according to claim 1, wherein said outer container is made of a self-shape retaining material so as not to be deformed by centrifugal force.

5. The centrifugal separation-use device according to claim 1, wherein said solution is blood.

6. The centrifugal separation-use device according to claim 1, wherein said target component is platelet-rich plasma.

7. The centrifugal separation-use device according to claim 1, wherein said solution is bone marrow fluid.

8. The centrifugal separation-use device according to claim 1, wherein said target component is stem cells.

* * * * *